(12) United States Patent
Launay et al.

(10) Patent No.: US 6,888,916 B2
(45) Date of Patent: May 3, 2005

(54) PREPROCESSING METHODS FOR ROBUST TRACKING OF CORONARY ARTERIES IN CARDIAC COMPUTED TOMOGRAPHY IMAGES AND SYSTEMS THEREFOR

(75) Inventors: Laurent Launay, Saint Rémy lès Chevreuse (FR); Renaud Capolunghi, Paris (FR); Jérôme Knoplioch, Neuilly sur Seine (FR)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 84 days.

(21) Appl. No.: 10/642,710

(22) Filed: Aug. 18, 2003

(65) Prior Publication Data
US 2005/0041769 A1 Feb. 24, 2005

(51) Int. Cl.⁷ .................................................. A61B 6/03
(52) U.S. Cl. ................................. 378/8; 378/4; 378/901
(58) Field of Search ........................... 378/4, 8, 15, 19, 378/901

(56) References Cited

U.S. PATENT DOCUMENTS 6,121,775 A * 9/2000 Pearlman ..................... 324/309
6,134,293 A 10/2000 Guendel
2003/0187358 A1 * 10/2003 Okerlund et al. ........... 600/443

* cited by examiner

Primary Examiner—David V Bruce
(74) Attorney, Agent, or Firm—Christopher L. Bernard, Esq.

(57) ABSTRACT

Preprocessing methods of this invention remove data relating to cavities of the heart, and improve density mix of parts left therein during CT imaging, so as to allow coronary arteries to be more accurately tracked with conventional tracking algorithms than currently possible. An embodiment comprises: obtaining an original CT voxel dataset comprising a plurality of voxels; creating a heart voxel dataset from the original voxel dataset comprising only voxels belonging to the heart; creating a heart minus cavities voxel dataset by removing voxels belonging to the left and right ventricles, the left and right atriums, and the aorta from the heart voxel dataset; enhancing predetermined voxels in the heart minus cavities voxel dataset to create an enhanced heart minus cavities voxel dataset; and mixing an intensity of the original CT voxel dataset with an intensity of the enhanced heart minus cavities voxel dataset to create the pre-processed voxel dataset.

24 Claims, 4 Drawing Sheets

PREPROCESSING METHODS FOR ROBUST TRACKING OF CORONARY ARTERIES IN CARDIAC COMPUTED TOMOGRAPHY IMAGES AND SYSTEMS THEREFOR

FIELD OF THE INVENTION

The present invention relates generally to methods and systems for the display of computed tomographic (CT) images. More specifically, the present invention relates to improved preprocessing methods and systems for robust tracking of coronary arteries in cardiac CT images. Even more specifically, the present invention relates to methodology that removes the cavities of the heart and improves the density mix of the parts therein during CT imaging so as to allow coronary arteries to be more accurately tracked than currently possible.

BACKGROUND OF THE INVENTION

Computed tomography (CT), sometimes called computed axial tomography (CAT) or CAT scan, uses special x-ray equipment to obtain image data from different angles around a person's body, and then uses computer processing of the data to create a two-dimensional cross-sectional image (i.e., slice) of the body tissues and organs that were scanned. CT imaging is particularly useful because it can show a combination of several different types of tissue (i.e., heart, lungs, stomach, colon, kidneys, liver, bone, blood vessels, muscles, etc.) with high spatial resolution and a great deal of clarity and contrast. Radiologists can interpret CT images to diagnose various injuries and illnesses, such as cardiovascular disease, trauma, cancer, and musculoskeletal disorders. CT images can also be used to aid in minimally invasive surgeries, and to allow for accurate planning and pinpointing of tumors for radiation treatment, among other things.

CT imaging allows structures within a body to be identified and delineated without superimposing other structures on the images created thereby. In a typical CT system, an x-ray source emits a beam that passes through a section of an object being imaged, typically a patient. After passing through the object and being more or less attenuated by the object, detectors receive the beam and measure the beam's intensity, which can vary since different parts of the body absorb and attenuate the x-rays differently.

Computed tomography is particularly useful in the medical field for analyzing tortuous structures such as airways, vessels, ducts or nerves, and thanks to advances in ECG-gated reconstruction techniques, CT can now provide quality images of the heart and coronary arteries. Conventional methods and apparatuses for imaging heart and coronary arteries use multiple oblique slices to analyze local segments of these structures. Although these conventional methods and apparatuses provide clear, undistorted pictures of short sections of tortuous structures, the views rarely encompass the full length thereof. Furthermore, when looking at axial CT slices, coronary arteries are often difficult to analyze because of the anatomy of the heart, the small size of the coronary arteries, and the complexity of the 3-dimensional trajectory of the coronary arteries.

Knowing the central path of coronary vessels allows one to provide advanced visualization modes like curved or lumen reformatted views, which display, on a two dimensional screen, reformatted views along the coronary vessels based on the computed central path thereof. Knowing the central path of coronary vessels also allows easier navigation in the vessel, vessel quantification, and better 3-dimensional visualization of the vessel's anatomy. Post-processing computation (i.e., estimation) of the central path of coronary vessels is currently possible after defining an upstream starting point and a downstream ending point for each vessel branch. However, existing coronary tracking techniques are not ideal, and often they do not accurately track the coronary arteries.

Designing a robust coronary artery tracking technique is challenging for a variety of reasons. The small size of coronary arteries leads to contrast variations and partial volume effects, especially in the presence of calcifications. Additionally, the trajectory of coronary arteries is complex. Furthermore, the coronary arteries are in close proximity to heart cavities (i.e., ventricles) and veins which, although they are usually larger and more uniform than the coronary arteries, generally have a similar gray level value in a CT image as the coronary arteries. As a result, vessel tracking techniques sometimes fail to properly image the vessel, and instead provide a path that goes through a vein or cavity instead of following the desired vessel. Since existing coronary tracking techniques have many drawbacks, it would be desirable to have improved coronary tracking techniques.

This invention provides preprocessing techniques that improve the tracking and imaging of coronary arteries by increasing the robustness of a vessel tracking algorithm for cardiac CT exams.

SUMMARY OF THE INVENTION

Accordingly, the above-identified shortcomings of existing coronary artery tracking techniques are overcome by embodiments of the present invention, which relates to improved coronary artery tracking techniques for the robust tracking of these arteries in CT images. Embodiments of this invention comprise preprocessing techniques that remove the cavities of the heart, and improve the density mix of the parts therein, during CT imaging so as to allow coronary arteries to be more accurately tracked than currently possible.

Embodiments of this invention comprise methods for obtaining a pre-processed voxel dataset for use in a tracking algorithm for accurately tracking coronary arteries in CT images. These methods comprise: obtaining an original CT voxel dataset comprising a plurality of voxels; creating a heart voxel dataset from the original CT voxel dataset comprising only voxels belonging to the heart; creating a heart minus cavities voxel dataset by removing voxels belonging to the left ventricle, the right ventricle, the left atrium, the right atrium, and the aorta from the heart voxel dataset; enhancing predetermined voxels in the heart minus cavities voxel dataset to create an enhanced heart minus cavities voxel dataset; and mixing an intensity of the original CT voxel dataset with an intensity of the enhanced heart minus cavities voxel dataset to create the pre-processed voxel dataset.

Other embodiments of this invention comprise methods for obtaining a pre-processed voxel dataset for use in tracking algorithms for accurately tracking coronary arteries in CT images. These methods comprise the steps of: obtaining an original CT dataset comprising a plurality of voxels; identifying the voxels in the original CT dataset belonging to a heart, a left ventricle, a right ventricle, a left atrium, a right atrium, and an aorta; removing from the original CT dataset the voxels belonging to the heart to create a heart voxel dataset; removing from the heart voxel dataset the voxels belonging to the left ventricle, the right ventricle, the left atrium, the right atrium, and the aorta to create a heart minus cavities voxel dataset; enhancing voxels belonging to vessels proximate the heart to create an enhanced heart minus cavities voxel dataset; and linearly mixing an x-ray intensity of the original CT dataset and an x-ray intensity of the enhanced heart minus cavities voxel dataset to create the pre-processed voxel dataset.

Yet other embodiments of this invention comprise systems for accurately tracking coronary arteries in CT images. These system comprise: a computed tomography apparatus capable of providing an original CT voxel dataset comprising a plurality of voxels; a means for creating a heart voxel dataset from the original CT voxel dataset comprising only voxels belonging to the heart; a means for creating a heart minus cavities voxel dataset by removing voxels belonging to the left ventricle, the right ventricle, the left atrium, the right atrium, and the aorta from the heart voxel dataset; a means for enhancing predetermined voxels in the heart minus cavities voxel dataset to create an enhanced heart minus cavities voxel dataset; and a means for mixing an intensity of the original CT voxel dataset with an intensity of the enhanced heart minus cavities voxel dataset to create the pre-processed voxel dataset.

Still other embodiments of this invention comprise systems for obtaining a pre-processed voxel dataset for use in tracking algorithms for accurately tracking coronary arteries in CT images. These system comprise: a computed tomography apparatus capable of providing an original CT dataset comprising a plurality of voxels; a means for identifying the voxels in the original CT dataset belonging to a heart, a left ventricle, a right ventricle, a left atrium, a right atrium, and an aorta; a means for removing from the original CT dataset the voxels belonging to the heart to create a heart voxel dataset; a means for removing from the heart voxel dataset the voxels belonging to the left ventricle, the right ventricle, the left atrium, the right atrium, and the aorta to create a heart minus cavities voxel dataset; a means for enhancing voxels belonging to vessels proximate the heart to create an enhanced heart minus cavities voxel dataset; and a means for linearly mixing an x-ray intensity of the original CT dataset and an x-ray intensity of the enhanced heart minus cavities voxel dataset to create the pre-processed voxel dataset.

The pre-processed voxel dataset is utilized as input in a vessel tracking algorithm. Enhancing predetermined voxels in the heart minus cavities voxel dataset comprises: dilating vessels proximate the heart; and enhancing intensities of the dilated vessels. Enhancing intensities of the dilated vessels comprises utilizing high pass gray-level filtering. Mixing the intensity of the original CT voxel dataset with the intensity of the enhanced heart minus cavities voxel dataset to create the pre-processed voxel dataset comprises utilizing the simple linear combination:

$$V_{output}(i) = \alpha * V_{filtered}(i) + (1-\alpha) * V_{original}(i)$$

wherein $V_{output}(i)$ is the pre-processed voxel dataset comprising a linear mix of x-ray intensities, $V_{original}(i)$ is the x-ray intensity of the original CT voxel dataset, and $V_{filtered}(i)$ is the x-ray intensity of the enhanced heart minus cavities voxel dataset, wherein $\alpha$ is about 0.7.

Further features, aspects and advantages of the present invention will be more readily apparent to those skilled in the art during the course of the following description, wherein references are made to the accompanying figures which illustrate some preferred forms of the present invention, and wherein like characters of reference designate like parts throughout the drawings.

DESCRIPTION OF THE DRAWINGS

The systems and methods of the present invention are described herein below with reference to various figures, in which.

DETAILED DESCRIPTION OF THE INVENTION

For the purposes of promoting an understanding of the invention, reference will now be made to some preferred embodiments of the present invention as illustrated in FIGS. 1–5 and specific language used to describe the same. The terminology used herein is for the purpose of description, not limitation. Specific structural and functional details disclosed herein are not to be interpreted as limiting, but merely as a basis for the claims as a representative basis for teaching one skilled in the art to variously employ the present invention. Any modifications or variations in the depicted support structures and methods, and such further applications of the principles of the invention as illustrated herein, as would normally occur to one skilled in the art, are considered to be within the spirit of this invention.

This invention relates to improved preprocessing methods and systems for the robust tracking of coronary arteries in cardiac CT images. The methodology of this invention removes the data relating to the cavities of the heart and improves the density mix of the parts therein during CT imaging so as to allow coronary arteries to be more accurately tracked with conventional tracking algorithms than currently possible.

Figure 1:
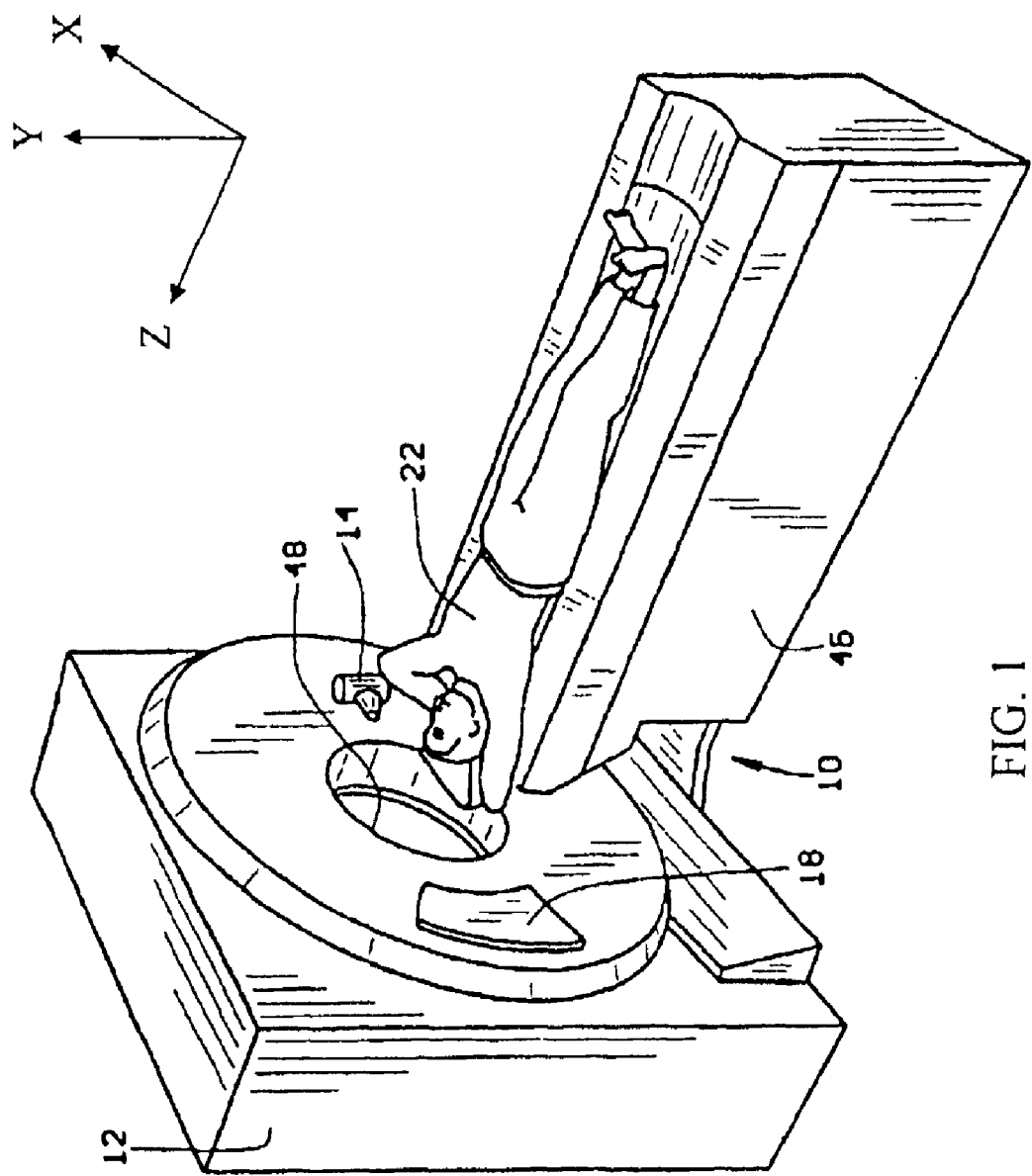
FIG. 1 is a schematic drawing showing one embodiment of a CT imaging system that may be utilized in embodiments of this invention.

Referring now to FIG. 1, there is shown a schematic diagram showing an exemplary CT imaging system 10 that may be utilized in embodiments of this invention. Such systems generally comprise a gantry 12, a gantry opening 48, and a table 46 upon which a patient 22 may lie. Gantry 12 comprises an x-ray source 14 that projects a beam of x-rays 16 toward an array of detector elements 18. During operation, gantry 12 rotates about a center of rotation 24 to obtain an image of one or more "slices" of an area of interest in patient 22. Generally, the array of detector elements 18 comprises a plurality of individual detector elements 20 that are arranged in a side-by-side manner in the form of an arc that is essentially centered on x-ray source 14. In multi-slice imaging systems, parallel rows of arrays of detector elements 18 can be arranged so that each row of detectors can be used to simultaneously generate multiple thin slice images through patient 22 in the X-Y plane. Each detector element in the array of detector elements 18 senses and detects the x-rays 16 that pass through an object, such as patient 22, and then creates an image therefrom. While this figure shows the x-ray source 14 and the array of detector elements 18 aligned along the X-axis, some CT imaging systems may align the x-ray source 14 and the array of detector elements 22 differently, such as along the Y-axis or anywhere else in the X-Y plane.

Figure 2:
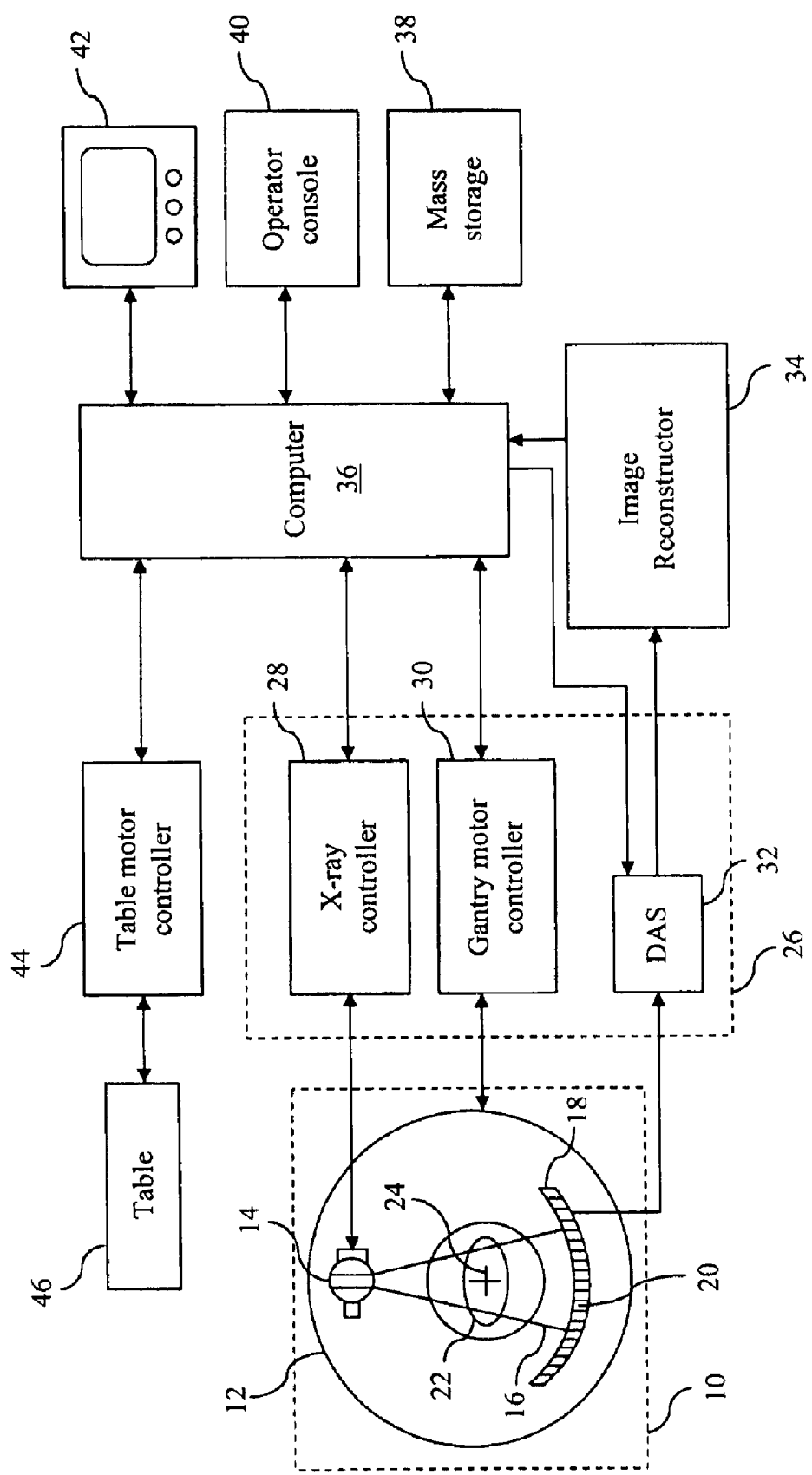
FIG. 2 is a schematic diagram showing the architecture of the CT imaging system shown in FIG. 1.

Referring now to FIG. 2, there is shown a schematic diagram showing the architecture of the CT imaging system shown in FIG. 1. The rotation of gantry 12 and the operation of x-ray source 14 are governed by a control mechanism 26 of CT imaging system 10. Control mechanism 26 includes an x-ray controller 28 that provides power and timing signals to x-ray source 14, and a gantry motor controller 30 that controls the rotational speed and position of gantry 12. A data acquisition system (DAS) 32 in control mechanism 26 samples analog data from the individual detector elements 20, and converts that analog data to digital signals for subsequent processing in accordance with the methods and systems of this invention. An image reconstructor 34 receives the sampled and digitized x-ray data from DAS 32 and performs high speed image reconstruction. The reconstructed image is then applied as input to a computer 36, which can store the image in a mass storage device 38. Computer 36 may also retrieve stored images from the mass storage device 38 for later viewing.

Computer 36 may also receive commands and scanning parameters from an operator via an operator console 40, which may comprise a keyboard, touchpad, or other suitable input device. An associated cathode ray tube display 42 (or other suitable display) may allow the operator to view the reconstructed image and other data from computer 36. The operator supplied commands and parameters may be used by computer 36 to provide control signals and information to DAS 32, x-ray controller 28 and gantry motor controller 30. Additionally, computer 36 may operate a table motor controller 44 which can control a motorized table 46, thereby allowing the patient 22 to be properly positioned within gantry 12 or moved therethrough. For example, table 46 may move portions of patient 22 through gantry opening 48 in the Z-direction.

Embodiments of the present invention may make use of software or firmware running on computer 36 to carry out the preprocessing of data in the methods and systems of this invention. A mouse or pointing device may be employed to facilitate the entry of data and/or image locations. Other embodiments of this invention may utilize a general purpose computer or workstation having a memory and/or printing capability for storing or printing images. Suitable memory devices are well known and include, but are not limited to, RAM, diskettes, hard drives and optical media. Embodiments using such stand-alone computers or workstations may receive data from CT imaging system 10 via conventional electronic storage media or via a conventional communications link, and images may then be reconstructed therefrom.

A CT image is made up of multiple x-ray absorption measurements around an object's periphery. The image is represented as a matrix of numbers, with each individual number in the image matrix representing a three-dimensional volume element in the scanned part, called a "voxel." To obtain a visual image, each voxel is represented as a two-dimensional picture element, or "pixel." Each pixel has a shade of gray representing the x-ray attenuation within the corresponding voxel.

Figure 3:
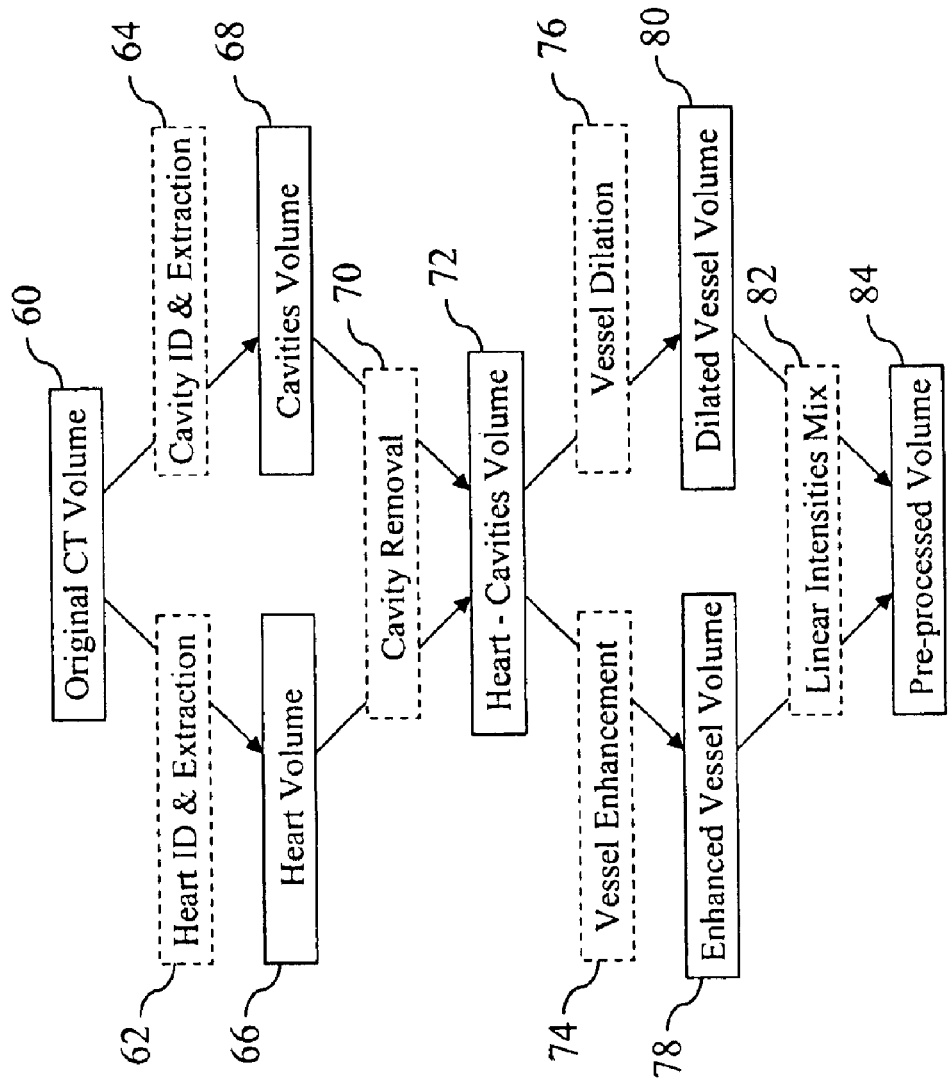
FIG. 3 is a flow diagram showing the steps that are performed in the preprocessing method of one embodiment of this invention.

An appreciation of this invention can be had by referring to FIG. 3, which shows the steps followed in one non-limiting embodiment of this invention. This invention comprises preprocessing techniques that take the original CT dataset and create a new 3-dimensional dataset therefrom, which can then be used as input in a vessel tracking algorithm. One embodiment comprises the preprocessing steps shown in FIG. 3. Initially, traditional CT techniques may be used to generate an original CT volume dataset 60. Thereafter, this invention extracts the heart 62 and cavities 64 data from the original dataset and creates two new volume datasets, with one comprising data only for the heart 66 and the other comprising data only for the heart cavities and aorta 68. Heart extraction 62 comprises identifying and removing from the original CT volume dataset 60 all voxels that are external to the heart (i.e., those voxels belonging to the lungs, ribs, etc.) to create the heart volume 66. Cavities extraction 64 comprises identifying and removing from the original CT volume dataset 60 those voxels that belong to the heart cavities (i.e., the left and right ventricle and atrium) and the aorta to create the cavities volume 68. Heart extraction 62 and cavities extraction 64 can be accomplished in any suitable manner, such as for example, by using a succession of simple binary mathematical morphology operations, such as for example: (1) thresholding to keep only the bone and contrast enhanced parts in the 3-D datasets; (2) selecting the largest connected components to get the cavities; and then (3) 3-D dilation to retrieve the muscle and coronaries surrounding the cavities and identify the heart. Once the heart volume 66 and cavities volume 68 are created, cavities volume 68 can be removed 70 from heart volume 66 to form a heart minus cavities volume 72. Removing the data that is not of interest (i.e., everything external to the heart, and even the aorta and heart cavities themselves) from the original CT volume dataset 60, reduces the number of voxels remaining to be processed, and thereby allows the computational speed of the tracking algorithm to be increased. Additionally, removing the unwanted data helps ensure that the tracking algorithm tracks within the vessels, since any possible paths through the cavities do not exist anymore. One possible drawback to this method, however, is that sometimes portions of the vessels that are very close to the cavities may also be removed from the heart minus cavities volume 72.

Once a heart minus cavities volume 72 is created, the vessels can then be enhanced 74, and the interior of the vessels can be dilated 76. Vessel enhancement processing 74 is intended to increase the intensity of the vessels, while lowering the intensity of other structures. Vessel enhancement may be accomplished using, for example, high pass gray-level filtering. The results thereof may then be stored in enhanced vessel volume 78. The interior of the vessels can also be dilated 76 to form dilated vessel volume 80. Vessel enhancement allows the vessel tracking algorithm to focus only on the vessels. However, sometimes vessels may be too close to the heart cavities to be adequately enhanced. Dilation of the vessels 76 allows the vessel voxels that may have otherwise been removed from the heart minus cavities volume 72, due to their proximity to the heart cavities, to be identified and added back in to the heart minus cavities volume 72.

Once an enhanced vessel volume 78 and a dilated vessel volume 80 are obtained, a linear mix of x-ray intensities 82 between the original CT volume 60 and the high pass filtered intensities can be obtained. When the intensity of some vessel portions has been lowered due to the techniques of this invention, the linear intensity mix 82 allows the original intensity of the vessel to be taken into account by the vessel tracking algorithm. The linear mix of intensities 82 may be obtained using a simple linear combination such as:

$$V_{output}(i) = \alpha * V_{filtered}(i) + (1-\alpha) * V_{original}(i)$$

where $V_{output}(i)$ is the linear mix of x-ray intensities, $V_{original}(i)$ is the x-ray intensity of the original CT volume, $V_{filtered}(i)$ is the x-ray intensity of the high pass filtered and enhanced volume, and α is a parameter to be adjusted experimentally. It has been found that a value of 0.7 for α yields good results in practice. Once the linear mix of x-ray intensities 82 is obtained, this constitutes the final preprocessed volume 84.

The interior vessel dilation 76 and final intensity mix 82 are performed to address the drawbacks that had been previously mentioned. Interior vessel dilation 76 and final intensity mix 82 ensure: (1) that portions of the vessels that may have been removed because of their close proximity to a cavity are added back in to the preprocessed volume, and (2) that the vessels that were not adequately enhanced remain in the final preprocessed volume 84.

The final preprocessed volume 84 may then be used as input into a vessel tracking algorithm, where centerline tracking of the vessels can then be had based on the combination of the original and high pass filtered intensities. Any conventional vessel tracking algorithm can be used to track the vessels accurately, once the preprocessing of this invention is accomplished and used as the input to the tracking algorithm. The tracking algorithm will identify the best cost path from a tracking point to a specific target. This cost function is defined to maximize the sum of values along the path. The minimization is performed using dynamic programming techniques.

Figure 5:
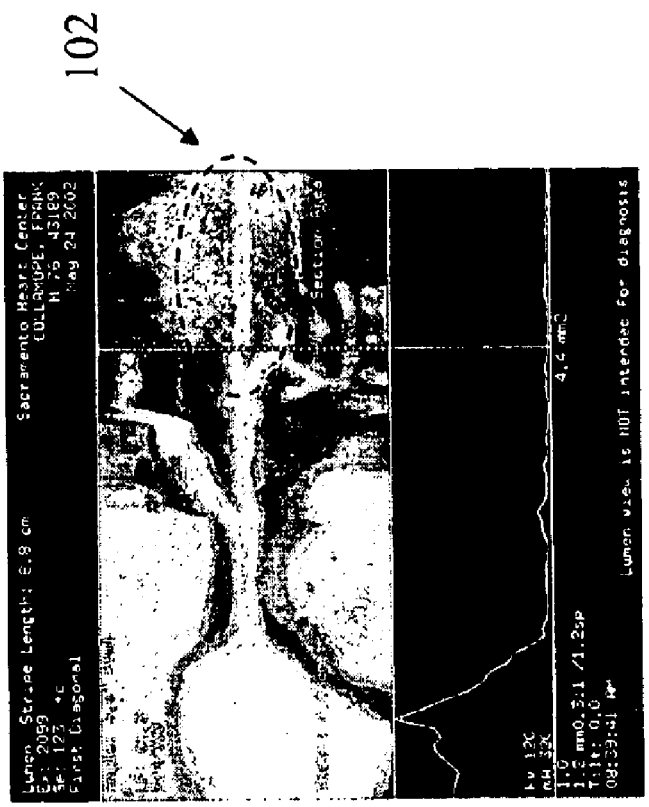
FIG. 5 is a CT photomicrograph image showing the tracking results that are obtained utilizing an embodiment of the cavities removal and density mixing methodology of this invention.
Figure 4:
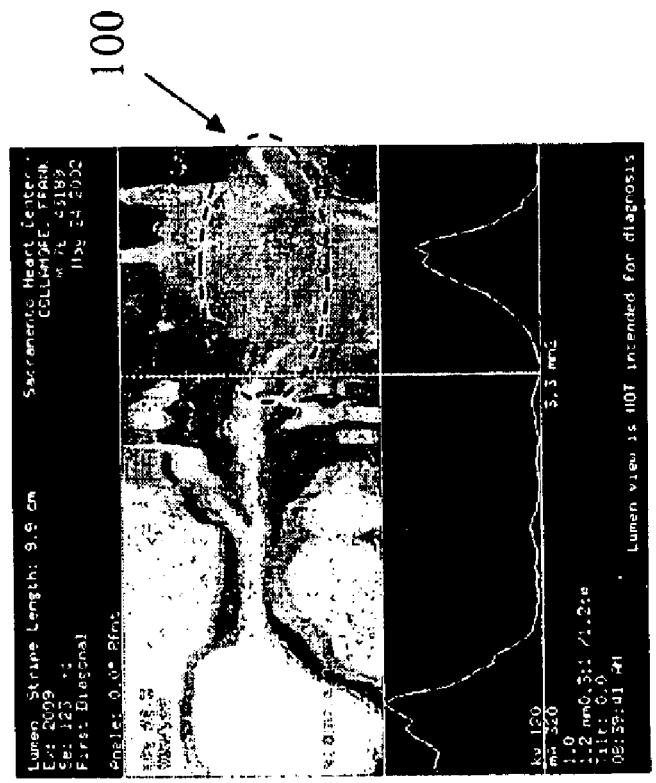
FIG. 4 is a CT photomicrograph image showing the tracking results that are obtained using conventional CT imaging methodology without utilizing the cavities removal and density mixing methodology of this invention.

Referring now to FIGS. 4 and 5, there are shown two images that illustrate the improved tracking techniques of this invention. FIG. 4 is a CT photomicrograph image showing the tracking results that are obtained using conventional CT imaging methodology, without utilizing the cavities removal and density mixing methodology of this invention. FIG. 5 is a CT photomicrograph image showing the tracking results that are obtained utilizing an embodiment of the cavities removal and density mixing methodology of this invention. As can be seen in FIG. 4, a vessel is running near a ventricle, and using a conventional tracking technique, the tracked path improperly crossed the ventricle 100 rather than going into the vessel. As seen here in FIG. 4, the vessel seems to end at the left side of the cavity, and then restart again at the right side of the cavity. This is because the conventional tracking technique missed this portion of the vessel and improperly tracked it through the cavity instead. In contrast, and as can be seen in FIG. 5, the pre-processing techniques of this invention allow the vessel to be properly tracked 102.

As described above, the techniques of this invention allow coronary arteries to be more accurately tracked than currently possible, with minimal disruption due to the heart cavities and aorta. Advantageously, since this invention more accurately tracks coronary arteries, less manual interaction is needed to correct a poorly tracked vessel path. Therefore, the techniques of this invention allow CT productivity to increase. Many other advantages will also be apparent to those skilled in the relevant art.

Various embodiments of this invention have been described in fulfillment of the various needs that the invention meets. It should be recognized that these embodiments are merely illustrative of the principles of various embodiments of the present invention. Numerous modifications and adaptations thereof will be apparent to those skilled in the art without departing from the spirit and scope of the present invention. For example, it will be appreciated by those skilled in the art that the techniques of this invention may be performed in numerous different ways without varying from the spirit and scope of this invention, and all such variations are intended to be covered herein. Thus, it is intended that the present invention cover all suitable modifications and variations as come within the scope of the appended claims and their equivalents.

What is claimed is:

1. A method for obtaining a pre-processed voxel dataset for use in a tracking algorithm for accurately tracking coronary arteries in CT images, the method comprising the steps of:

obtaining an original CT voxel dataset comprising a plurality of voxels;

creating a heart voxel dataset from the original CT voxel dataset comprising only voxels belonging to the heart;

creating a heart minus cavities voxel dataset by removing voxels belonging to the left ventricle, the right ventricle, the left atrium, the right atrium, and the aorta from the heart voxel dataset;

enhancing predetermined voxels in the heart minus cavities voxel dataset to create an enhanced heart minus cavities voxel dataset; and mixing an intensity of the original CT voxel dataset with an intensity of the enhanced heart minus cavities voxel dataset to create the pre-processed voxel dataset.

2. The method of claim 1, wherein the pre-processed voxel dataset is utilized as input in a vessel tracking algorithm.

3. The method claim 1, wherein enhancing predetermined voxels in the heart minus cavities voxel dataset comprises:

dilating vessels proximate the heart; and enhancing intensities of the dilated vessels.

4. The method of claim 3, wherein enhancing intensities of the dilated vessels comprises utilizing high pass gray-level filtering.

5. The method of claim 1, wherein mixing the intensity of the original CT voxel dataset with the intensity of the enhanced heart minus cavities voxel dataset to create the pre-processed voxel dataset comprises utilizing the simple linear combination:

$$V_{output}(i) = \alpha * V_{filtered}(i) + (1-\alpha) * V_{original}(i)$$

wherein $V_{output}(i)$ is the pre-processed voxel dataset comprising a linear mix of x-ray intensities, $V_{original}(i)$ is the x-ray intensity of the original CT voxel dataset, and $V_{filtered}(i)$ is the x-ray intensity of the enhanced heart minus cavities voxel dataset.

6. The method of claim 5, wherein α is about 0.7.

7. A method for obtaining a pre-processed voxel dataset for use in tracking algorithms for accurately tracking coronary arteries in CT images, the method comprising the steps of:

obtaining an original CT dataset comprising a plurality of voxels;

identifying the voxels in the original CT dataset belonging to a heart, a left ventricle, a right ventricle, a left atrium, a right atrium, and an aorta;

removing from the original CT dataset the voxels belonging to the heart to create a heart voxel dataset;

removing from the heart voxel dataset the voxels belonging to the left ventricle, the right ventricle, the left atrium, the right atrium, and the aorta to create a heart minus cavities voxel dataset;

enhancing voxels belonging to vessels proximate the heart to create an enhanced heart minus cavities voxel dataset; and linearly mixing an x-ray intensity of the original CT dataset and an x-ray intensity of the enhanced heart minus cavities voxel dataset to create the pre-processed voxel dataset.

8. The method of claim 7, wherein the pre-processed voxel dataset is utilized as input in a vessel tracking algorithm.

9. The method of claim 7, wherein enhancing voxels belonging to vessels proximate the heart to create the enhanced heart minus cavities voxel dataset comprises:

dilating vessels proximate the heart; and enhancing intensities of the dilated vessels.

10. The method of claim 9, wherein enhancing intensities of the dilated vessels comprises utilizing high pass gray-level filtering.

11. The method of claim 7, wherein linearly mixing the x-ray intensity of the original CT dataset with the x-ray intensity of the enhanced heart minus cavities voxel dataset to create the pre-processed voxel dataset comprises utilizing the simple linear combination:

$$V_{output}(i)=\alpha*V_{filtered}(i)+(1-\alpha)*V_{original}(i)$$

wherein $V_{output}(i)$ is the pre-processed voxel dataset comprising a linear mix of x-ray intensities, $V_{original}(i)$ is the x-ray intensity of the original CT dataset, and $V_{filtered}(i)$ is the x-ray intensity of the enhanced heart minus cavities voxel dataset.

12. The method of claim 11, wherein $\alpha$ is about 0.7.

13. A system for accurately tracking coronary arteries in CT images, the system comprising:

a computed tomography apparatus capable of providing an original CT voxel dataset comprising a plurality of voxels;

a means for creating a heart voxel dataset from the original CT voxel dataset comprising only voxels belonging to the heart;

a means for creating a heart minus cavities voxel dataset by removing voxels belonging to the left ventricle, the right ventricle, the left atrium, the right atrium, and the aorta from the heart voxel dataset;

a means for enhancing predetermined voxels in the heart minus cavities voxel dataset to create an enhanced heart minus cavities voxel dataset; and a means for mixing an intensity of the original CT voxel dataset with an intensity of the enhanced heart minus cavities voxel dataset to create the pre-processed voxel dataset.

14. The system of claim 13, wherein the pre-processed voxel dataset is utilized as input in a vessel tracking algorithm.

15. The system claim 13, wherein the means for enhancing predetermined voxels in the heart minus cavities voxel dataset comprises:

a means for dilating vessels proximate the heart; and a means for enhancing intensities of the dilated vessels.

16. The system of claim 15, wherein the means for enhancing intensities of the dilated vessels comprises a means for utilizing high pass gray-level filtering.

17. The system of claim 13, wherein the means for mixing the intensity of the original CT voxel dataset with the intensity of the enhanced heart minus cavities voxel dataset to create the pre-processed voxel dataset comprises a means for utilizing the simple linear combination:

$$V_{output}(i)=\alpha*V_{filtered}(i)+(1-\alpha)*V_{original}(i)$$

wherein $V_{output}(i)$ is the pre-processed voxel dataset comprising a linear mix of x-ray intensities, $V_{original}(i)$ is the x-ray intensity of the original CT voxel dataset, and $V_{filtered}(i)$ is the x-ray intensity of the enhanced heart minus cavities voxel dataset.

18. The system of claim 17, wherein $\alpha$ is about 0.7.

19. A system for obtaining a pre-processed voxel dataset for use in tracking algorithms for accurately tracking coronary arteries in CT images, the system comprising:

a computed tomography apparatus capable of providing an original CT dataset comprising a plurality of voxels;

a means for identifying the voxels in the original CT dataset belonging to a heart, a left ventricle, a right ventricle, a left atrium, a right atrium, and an aorta;

a means for removing from the original CT dataset the voxels belonging to the heart to create a heart voxel dataset;

a means for removing from the heart voxel dataset the voxels belonging to the left ventricle, the right ventricle, the left atrium, the right atrium, and the aorta to create a heart minus cavities voxel dataset;

a means for enhancing voxels belonging to vessels proximate the heart to create an enhanced heart minus cavities voxel dataset; and a means for linearly mixing an x-ray intensity of the original CT dataset and an x-ray intensity of the enhanced heart minus cavities voxel dataset to create the pre-processed voxel dataset.

20. The system of claim 19, wherein the pre-processed voxel dataset is utilized as input in a vessel tracking algorithm.

21. The system of claim 19, wherein the means for enhancing voxels belonging to vessels proximate the heart to create the enhanced heart minus cavities voxel dataset comprises:

a means for dilating vessels proximate the heart; and a means for enhancing intensities of the dilated vessels.

22. The system of claim 21, wherein the means for enhancing intensities of the dilated vessels comprises a means for utilizing high pass gray-level filtering.

23. The system of claim 19, wherein the means for linearly mixing the x-ray intensity of the original CT dataset with the x-ray intensity of the enhanced heart minus cavities voxel dataset to create the pre-processed voxel dataset comprises a means for utilizing the simple linear combination:

$$V_{output}(i)=\alpha*V_{filtered}(i)+(1-\alpha)*V_{original}(i)$$

wherein $V_{output}(i)$ is the pre-processed voxel dataset comprising a linear mix of x-ray intensities, $V_{original}(i)$ is the x-ray intensity of the original CT dataset, and $V_{filtered}(i)$ is the x-ray intensity of the enhanced heart minus cavities voxel dataset.

24. The system of claim 23, wherein $\alpha$ is about 0.7.

* * * * *